US011311514B2

(12) United States Patent
Oh et al.

(10) Patent No.: US 11,311,514 B2
(45) Date of Patent: Apr. 26, 2022

(54) PHARMACEUTICAL COMPOSITION FOR PREVENTING OR TREATING PRURITUS, CONTAINING PYRAZOLE DERIVATIVE AS ACTIVE INGREDIENT, AND SCREENING METHOD FOR DETECTING SAME

(71) Applicants: Seoul National University R&DB Foundation, Seoul (KR); Kanzen Co., Ltd., Seoul (KR)

(72) Inventors: Uhtaek Oh, Gyeonggi-do (KR); Ji Yeong Lee, Seoul (KR); Sung Ae An, Gyeonggi-do (KR)

(73) Assignees: Seoul National University R&DB Foundation, Seoul (KR); Kanzen Co., Ltd., Seoul (KR)

( * ) Notice: Subject to any disclaimer, the term of this patent is extended or adjusted under 35 U.S.C. 154(b) by 416 days.

(21) Appl. No.: 16/491,449

(22) PCT Filed: Mar. 6, 2018

(86) PCT No.: PCT/KR2018/002626
§ 371 (c)(1),
(2) Date: Oct. 24, 2019

(87) PCT Pub. No.: WO2018/164442
PCT Pub. Date: Sep. 13, 2018

(65) Prior Publication Data
US 2020/0246309 A1 Aug. 6, 2020

(30) Foreign Application Priority Data
Mar. 6, 2017 (KR) ........................ 10-2017-0028220
Oct. 11, 2017 (KR) ........................ 10-2017-0130797

(51) Int. Cl.
*A61K 31/415* (2006.01)
*A61P 17/04* (2006.01)

(52) U.S. Cl.
CPC ............ *A61K 31/415* (2013.01); *A61P 17/04* (2018.01)

(58) Field of Classification Search
CPC .............................. A61K 31/415; A61P 17/04
See application file for complete search history.

(56) References Cited

U.S. PATENT DOCUMENTS 5,624,941 A 4/1997 Barth et al.

FOREIGN PATENT DOCUMENTS

| JP | 06-073014 A | 3/1994 |
| WO | 9841519 A1 | 9/1998 |
| WO | 2006062097 A1 | 6/2006 |
| WO | 2010108059 A1 | 9/2010 |
| WO | 2014069554 A1 | 5/2014 |

OTHER PUBLICATIONS

Bandell et al., "Itching for Insight", Cell, vol. 139, pp. 1224-1226 (2009).
Dong et al., "A Diverse Family of GPCRs Expressed in Specific Subses of Nociceptive Sensory Neurons", Cell, vol. 106, pp. 619-632 (2001).
Liu et al., "Sensory Neuron-Specific GPCR Mrgprs Are Itch Receptors Mediating Chloroquine-Induced Pruritus", Cell, vol. 139, pp. 1353-1365 (2009).
Miyamoto et al., "Itch-Associated Response Induced by Experimental Dry Skin in Mice", Jpn. J. Pharmacol, vol. 88, pp. 285-292 (2002).
Ohsawa et al., "The Role of Histamine H1 and H4 Receptors in Atopic Dermatitis: From Basic Research to Clinical Study", Allergology International, vol. 63, pp. 533-542 (2014).
Sakai et al., "Mouse model of imiquimod-induced psoriatic itch", The International Association for the Study of Pain, vol. 157, pp. 2536-2543 (2016).
CAS Registry No. 1023499-28-6, STN Database Registry (2008).
International Search Report for PCT/KR2018/002626, dated Jun. 15, 2018.
Kuraishi. "Mechanisms of itch and the pharmacology of anti-pruritic agents." Nihon yakurigaku zasshi. Folia pharmacologica Japonica 139.4 (2012): 160-164.
Satoh et al. "Clinical Practice Guideline for the Pruritus cutaneus universalis." Jpn J Dermatol 122 (2012): 267-80.

*Primary Examiner* — Theodore R. Howell
(74) *Attorney, Agent, or Firm* — Caesar Rivise, PC

(57) ABSTRACT

The present invention relates to a pharmaceutical composition for preventing or treating pruritus, containing a pyrazole derivative as an active ingredient, and a screening method for detecting the same. A pharmaceutical composition for preventing or treating pruritus, according to the present invention, can relieve the symptoms of pruritus by inhibiting the activity of intracellular Mrgpr X1, and can relieve the symptoms of pruritus by inhibiting the activity of intracellular hH1R, thereby being usable also as a medicine for preventing or treating histamine-mediated pruritus. In addition, it has been confirmed through dry skin mouse model experimentation that the composition also has significant alleviation effects on dry skin, thereby being usable as a medicine for treating dry skin. Furthermore, the pharmaceutical composition according to the present invention can relieve the symptoms of pruritus caused by psoriasis, thereby being usable also as a medicine for treating psoriasis. Moreover, the pharmaceutical composition according to the present invention can maintain stable activity, even during in vivo drug administration, without causing adverse reactions.

4 Claims, 10 Drawing Sheets

PHARMACEUTICAL COMPOSITION FOR PREVENTING OR TREATING PRURITUS, CONTAINING PYRAZOLE DERIVATIVE AS ACTIVE INGREDIENT, AND SCREENING METHOD FOR DETECTING SAME

CROSS-REFERENCE TO RELATED APPLICATIONS

This application is a U.S. national phase of PCT/KR2018/002626, filed Mar. 6, 2018, and claims priority to KR 10-2017-0028220, filed Mar. 6, 2017, and KR 10-2017-0130767, filed Oct. 11, 2017, the contents of which applications are incorporated herein by reference in their entireties for all purposes.

BACKGROUND OF THE INVENTION

1. Field of the Invention

The present invention relates to a pharmaceutical composition for preventing or treating pruritus, containing a pyrazole derivative as an active ingredient, and a screening method for detecting the same.

2. Description of the Related Art

Pruritus (or itch) is a noticeable symptom appearing on whole body in various skin disease cases. Pruritus causes itching to protect the skin from bugs, toxic plants or other harmful stimuli. However, pruritus does not always play such a beneficial role as the above. Chronic itch accompanies eczema, kidney disease, liver cirrhosis and skin diseases including some cancers. Many neurological diseases also cause severe itching, which are exemplified by including multiple sclerosis, diabetic neuropathy and postherpetic neuralgia (herpes zoster), etc. Pruritus is developed by sensory nerve cells and these cells are known to have a cell body in the dorsal root ganglion.

It is known that various types of pruritus are mediated by histamine (histaminergic pruritus).

Chloroquine, an antimalarial agent, is known to cause histamine-independent pruritus (non-histaminergic pruritus).

Mas-related G protein-coupled receptors (Mrgprs) are known as non-histaminergic pruritus receptors as GPCR (G protein-coupled receptors) expressed only in peripheral sensory neurons. These receptors are found in various tissues in adults, especially in neurons (Dong et al. 2001). Among them, Mrgpr X1 is distributed in the human dorsal root ganglion.

Histaminergic pruritus is known to be protected by human histamine receptor 1 antagonist (2009 Sensory neuron-specific GPCR Mrgprs are itch receptors mediating chloroquine-induced pruritus. Cell 139, 1353-1365 (2009)). However, the antagonist has no effect on non-histaminergic pruritus. Allergic itch is mediated by histamine, which takes only one third of total pruritus. Thus, allergic itch can be treated with antihistamines, but most itches cannot be treated with antihistamines.

As a treatment agent for pruritus, preparations for cooling skin comprising calamine lotion or 1% menthol lotion, steroids, and antihistamines are currently used. However, those preparations for cooling skin have only a temporary effect. On the other hand, steroids demonstrate a strong anti-inflammatory activity, so that they are excellent in alleviating the symptoms of various diseases such as joint disease, cerebrovascular disease, inflammatory disease and allergic disease, but are limited in use because of their side effects according to long term administration or overdose. Antihistamines are mainly formulated for oral administration. In general, drugs that inhibit only H1 receptor involved directly in pruritus have been developed. However, these drugs are also limited in use because they cause such side effects as overall decline of cognitive abilities and motor nerves. As explained above, there is no universal treatment method for pruritus, yet. Therefore, it is required to develop a safe and effective drug for pruritus.

Thus, the present inventors have studied to develop a safe and effective therapeutic agent which is not only effective in treating histaminergic pruritus but also effective in non-histaminergic pruritus. In the course of the study, the present inventors confirmed that a pyrazole derivative compound was effective in inhibiting the activities of Mrgpr X1 and hH1R (human histamine receptor subtype1), leading to the completion of the present invention.

SUMMARY OF THE INVENTION

It is an object of the present invention to provide a pharmaceutical composition for preventing or treating pruritus.

It is another object of the present invention to provide a health functional food composition for preventing or treating pruritus.

It is also an object of the present invention to provide a screening method of a compound for preventing or treating pruritus.

To achieve the above objects, the present invention provides a pharmaceutical composition comprising a compound represented by formula 1 below or a pharmaceutically acceptable salt thereof as an active ingredient for preventing or treating pruritus.

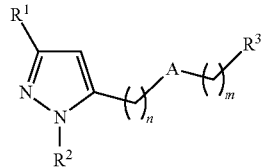

[Formula 1]

(In formula 1,
$R^1$, $R^2$, $R^3$, A, m and n are as defined in this specification.)

The present invention also provides a health functional food composition comprising a compound represented by formula 1 below or a pharmaceutically acceptable salt thereof as an active ingredient for preventing or alleviating pruritus.

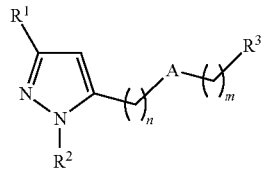

[Formula 1]

(In formula 1,
$R^1$, $R^2$, $R^3$, A, m and n are as defined in this specification.)

Further, the present invention provides a screening method of a compound for preventing or treating pruritus, which comprises the following steps:

treating a pruritus-inducing substance to cells expressing MRGPR X1 (Mas-related G protein-coupled receptor), and culturing the cells (step 1); and treating a candidate material to the pruritus-induced cells, and measuring the inhibition of MRGPR X1 activity (step 2).

In addition, the present invention provides a screening method of an active material for preventing or treating pruritus, which comprises the following steps:

treating a pruritus-inducing substance to cells expressing hH1R (human Histamine 1 Receptor), and culturing the cells (step 1); and treating a candidate material to the pruritus-induced cells, and measuring the inhibition of hH1R activity (step 2).

Advantageous Effect

The pharmaceutical composition for preventing or treating pruritus according to the present invention can be effectively used as a preventive or therapeutic agent for non-histaminergic pruritus because it can relieve the symptoms of pruritus by inhibiting the activity of intracellular Mrgpr X1. The pharmaceutical composition for preventing or treating pruritus according to the present invention can be effectively used as a preventive or therapeutic agent for histaminergic pruritus because it can relieve the symptoms of pruritus by inhibiting the activity of intracellular hH1R. In addition, it has been confirmed through dry skin mouse model experimentation that the composition also has significant alleviation effects on dry skin, thereby being usable as a medicine for treating dry skin. Furthermore, the pharmaceutical composition according to the present invention can relieve the symptoms of pruritus caused by psoriasis, thereby being usable also as a medicine for treating psoriasis. Moreover, the pharmaceutical composition according to the present invention can maintain stable activity, even during in vivo drug administration, without causing adverse reactions.

DESCRIPTION OF THE PREFERRED EMBODIMENTS

Figure 1:
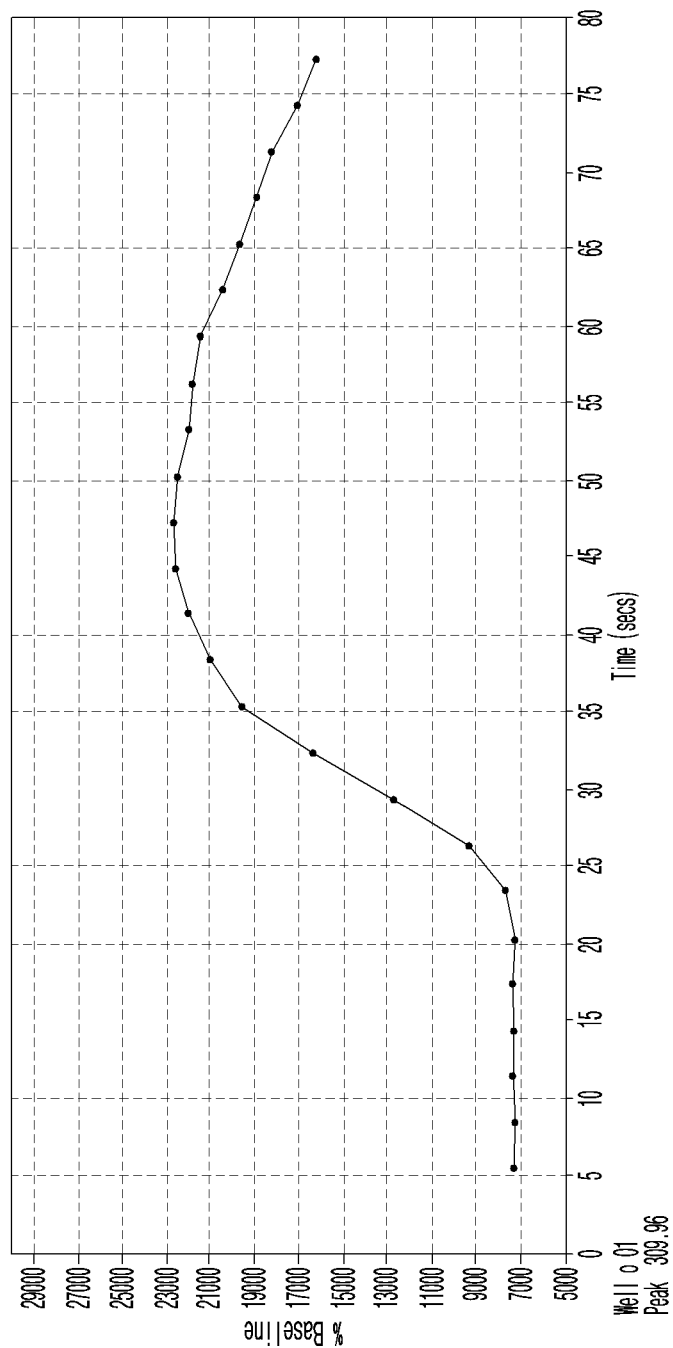
FIG. 1 is a graph showing the results of fluorescence analysis performed after treating Mrgpr X1 cells with chloroquine alone.

Hereinafter, the present invention is described in detail.

The present invention provides a pharmaceutical composition comprising a compound represented by formula 1 below or a pharmaceutically acceptable salt thereof as an active ingredient for preventing or treating pruritus.

[Formula 1]

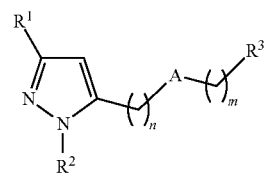

In formula 1 above, $R^1$ and $R^2$ are independently straight or branched $C_1$-$C_6$ alkyl, straight or branched $C_1$-$C_6$ alkoxy, —$NO_2$, —$NR^4R^5$ or nonsubstituted or substituted $C_6$-$C_{12}$ aryl, wherein the substituted $C_6$-$C_{12}$ aryl can be substituted with one or more substituents selected from the group consisting of halogen, straight or branched $C_1$-$C_6$ alkyl, straight or branched $C_1$-$C_6$ alkoxy, —$NO_2$ and —$NR^4R^5$, at this time, $R^4$ and $R^5$ are independently hydrogen or straight or branched $C_1$-$C_6$ alkyl;

$R^3$ is hydrogen, —(C=O)$OR^6$ or nonsubstituted or substituted 3-10 membered heterocycloalkyl or heterocycloalkenyl containing one or more heteroatoms selected from the group consisting of N, O and S, at this time, $R^6$ can be hydrogen or straight or branched $C_1$-$C_6$ alkyl, wherein the substituted heterocycloalkyl or heterocycloalkenyl can be substituted with one or more substituents selected from the group consisting of halogen, straight or branched $C_1$-$C_6$ alkyl and straight or branched $C_1$-$C_6$ alkoxy;

A is —NH—, —O—, —S—, —(C=O)NH—, —NH(C=O)—, —(C=O)O— or —O(C=O)—; and m and n can independently be integers of 0-8.

In addition, in formula 1 above, $R^1$ and $R^2$ are independently straight or branched $C_1$-$C_3$ alkyl, straight or branched $C_1$-$C_3$ alkoxy, —$NO_2$, —$NR^4R^5$ or nonsubstituted or substituted $C_6$-$C_{10}$ aryl, wherein the substituted $C_6$-$C_{10}$ aryl can be substituted with one or more substituents selected from the group consisting of halogen, straight or branched $C_1$-$C_3$ alkyl, straight or branched $C_1$-$C_3$ alkoxy, —$NO_2$ and —$NR^4R^5$, at this time, $R^4$ and $R^5$ are independently hydrogen or straight or branched $C_1$-$C_3$ alkyl;

$R^3$ is hydrogen, —(C=O)$OR^6$ or nonsubstituted or substituted 3-8 membered heterocycloalkyl or heterocycloalkenyl containing one or more heteroatoms selected from the group consisting of N, O and S, at this time, $R^6$ can be hydrogen or straight or branched $C_1$-$C_3$ alkyl, wherein the substituted heterocycloalkyl or heterocycloalkenyl can be substituted with one or more substituents selected from the group consisting of halogen, straight or branched $C_1$-$C_3$ alkyl and straight or branched $C_1$-$C_3$ alkoxy;

A is —NH—, —O—, —S—, —(C=O)NH—, —NH(C=O)—, —(C=O)O— or —O(C=O)—; and m and n can independently be integers of 0-6.

Further, in formula 1 above, $R^1$ and $R^2$ are independently straight or branched $C_1$-$C_3$ alkyl, —$NO_2$, or nonsubstituted or substituted phenyl, wherein the substituted phenyl can be substituted with one or more substituents selected from the group consisting of straight or branched $C_1$-$C_3$ alkyl, straight or branched $C_1$-$C_3$ alkoxy and —$NO_2$;

$R^3$ is hydrogen, —(C=O)$OR^6$ or nonsubstituted or substituted 5-7 membered heterocycloalkyl containing one or more heteroatoms selected from the group consisting of N, O and S, at this time, the substituted heterocycloalkyl can be substituted with one or more straight or branched $C_1$-$C_3$ alkyl groups;

A is —(C=O)NH—, —NH(C=O)—, —(C=O)O— or —O(C=O)—; and m and n can independently be integers of 0-5.

Moreover, in formula 1 above, $R^1$ and $R^2$ are independently methyl or nonsubstituted or substituted phenyl, wherein the substituted phenyl can be substituted with one or more substituents selected from the group consisting of methyl, methoxy and —$NO_2$;

$R^3$ is —(C=O)OH or piperidinyl substituted with one or more methyl groups;

A is —(C=O)NH— or —NH(C=O)—; and m and n can independently be integers of 0-3.

The said pruritus can be histaminergic pruritus, non-histaminergic pruritus, pruritus induced by chloroquine, pruritus induced by dry skin or psoriatic pruritus (pruritus induced by psoriasis). The pruritus can also be induced by neurodermatitis, contact dermatitis, seborrheic dermatitis, autosensitized dermatitis, caterpillar dermatitis, sebum deficiency (asteatosis), senile pruritus skin, insect bites, photosensitive dermatitis, urticaria, prurigo, herpes, impetigo, eczema, tinea, lichen, scabies or acne vulgaris. At this time, in the case of histaminergic pruritus, the pharmaceutical composition of the present invention can be effective in treating or preventing pruritus by blocking the activity of histamine via reversible/competitive antagonism against hH1R (human Histamine 1 Receptor).

The pharmaceutical composition of the present invention can also be effective in treating or preventing pruritus induced by chloroquine by blocking the activity of chloroquine via reversible/competitive antagonism against MRGPR X1.

The pharmaceutically acceptable salt of the compound of formula 1 can be prepared by the conventional method known to those in the art. For example, the pharmaceutically acceptable salt includes salts of inorganic acids such as hydrochloric acid, bromic acid, sulfuric acid, sodium hydrogen sulfate, phosphoric acid, nitric acid and carbonic acid; salts of organic acids such as formic acid, acetic acid, propionic acid, oxalic acid, succinic acid, benzoic acid, citric acid, maleic acid, malonic acid, tartaric acid, gluconic acid, lactic acid, gestyic acid, fumaric acid, lactobionic acid, salicylic acid and acetylsalicylic acid (aspirin); salts of amino acids such as glycine, alanine, vanillin, isoleucine, serine, cysteine, cystine, aspartic acid, glutamine, lysine, arginine, tyrosine and proline; salts of sulfonic acids such as methanesulfonic acid, ethanesulfonic acid, benzenesulfonic acid and toluenesulfonic acid; metal salts generated by reaction with alkali metals such as sodium and potassium; or ammonium ion salts.

The acid addition salt can be prepared by the conventional method known to those in the art. For example, the derivative represented by formula 1 is dissolved in an organic solvent such as methanol, ethanol, acetone, methylenechloride and acetonitrile, to which organic acid or inorganic acid is added to induce precipitation. Then, the precipitate is filtered and dried to give the salt. Or the solvent and the excessive acid are distilled under reduced pressure, followed by drying and crystallization in an organic solvent to give the salt.

In addition, a pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

Furthermore, the compound represented by formula 1 can be used in the form of solvates, optical isomers, hydrates, etc., which may be prepared therefrom, as well as the pharmaceutically acceptable salts thereof.

The pharmaceutical composition of the present invention can be formulated by adding non-toxic and pharmaceutically acceptable carriers, adjuvants and excipients according to the conventional methods. For example, the pharmaceutical composition of the present invention can be formulated for oral or parenteral administration in the forms of tablets, capsules, troches, solutions and suspensions, etc.

The compound represented by formula 1 or the pharmaceutically acceptable salt thereof can be administered in various oral and parenteral formulations during clinical administration. When the compound represented by formula 1 or the pharmaceutically acceptable salt thereof is formulated, generally used diluents or excipients such as fillers, extenders, binders, wetting agents, disintegrating agents and surfactants are used. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc., can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

To prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or a suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

In addition, the excipients that can be used in the pharmaceutical composition according to the present invention include sweeteners, binders, solubilizers, dissolution aids, wetting agents, emulsifiers, isotonic agents, adsorbents, disintegrants, antioxidants, preservatives, lubricants, fillers, fragrances, etc. For example, lactose, dextrose, sucrose, mannitol, sorbitol, cellulose, glycine, silica, talc, stearic acid, sterin, magnesium stearate, magnesium aluminum silicate, starch, gelatin, tragacanth rubber, alginic acid, sodium alginate, methyl cellulose, sodium carboxylmethyl cellulose, agar, water, ethanol, polyethylene glycol, polyvinylpyrrolidone, sodium chloride, calcium chloride, orange essence, strawberry essence, vanilla flavor and the like can be used as the excipients.

The effective dosage of the pharmaceutical composition of the present invention can be determined according to age, weight, gender, administration method, health condition, and severity of disease.

The dosage is generally 0.01~5000 mg/day based on an adult patient weighing 70 kg, which can be administered once or several times a day at intervals of a certain time depending on the judgment of a doctor or a pharmacist.

The present invention also provides a health functional food composition comprising a compound represented by formula 1 below or a pharmaceutically acceptable salt thereof as an active ingredient for preventing or alleviating pruritus.

[Formula 1]

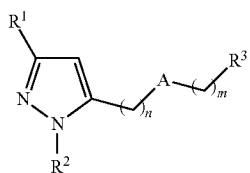

In formula 1 above, $R^1$ and $R^2$ are independently straight or branched $C_1$-$C_6$ alkyl, straight or branched $C_1$-$C_6$ alkoxy, —$NO_2$, —$NR^4R^5$ or nonsubstituted or substituted $C_6$-$C_{12}$ aryl, wherein the substituted $C_6$-$C_{12}$ aryl can be substituted with one or more substituents selected from the group consisting of halogen, straight or branched $C_1$-$C_6$ alkyl, straight or branched $C_1$-$C_6$ alkoxy, —$NO_2$ and —$NR^4R^5$, at this time, $R^4$ and $R^5$ are independently hydrogen or straight or branched $C_1$-$C_6$ alkyl;

$R^3$ is hydrogen, —(C=O)$OR^6$ or nonsubstituted or substituted 3-10 membered heterocycloalkyl or heterocycloalkenyl containing one or more heteroatoms selected from the group consisting of N, O and S, at this time, $R^6$ can be hydrogen or straight or branched $C_1$-$C_6$ alkyl, wherein the substituted heterocycloalkyl or heterocycloalkenyl can be substituted with one or more substituents selected from the group consisting of halogen, straight or branched $C_1$-$C_6$ alkyl and straight or branched $C_1$-$C_6$ alkoxy;

A is —NH—, —O—, —S—, —(C=O)NH—, —NH(C=O)—, —(C=O)O— or —O(C=O)—; and m and n can independently be integers of 0-8.

In addition, in formula 1 above, $R^1$ and $R^2$ are independently straight or branched $C_1$-$C_3$ alkyl, straight or branched $C_1$-$C_3$ alkoxy, —$NO_2$, —$NR^4R^5$ or nonsubstituted or substituted $C_6$-$C_{10}$ aryl, wherein the substituted $C_6$-$C_{10}$ aryl can be substituted with one or more substituents selected from the group consisting of halogen, straight or branched $C_1$-$C_3$ alkyl, straight or branched $C_1$-$C_3$ alkoxy, —$NO_2$ and —$NR^4R^5$, at this time, $R^4$ and $R^5$ are independently hydrogen or straight or branched $C_1$-$C_3$ alkyl;

$R^3$ is hydrogen, —(C=O)$OR^6$ or nonsubstituted or substituted 3-8 membered heterocycloalkyl or heterocycloalkenyl containing one or more heteroatoms selected from the group consisting of N, O and S, at this time, $R^6$ can be hydrogen or straight or branched $C_1$-$C_3$ alkyl, wherein the substituted heterocycloalkyl or heterocycloalkenyl can be substituted with one or more substituents selected from the group consisting of halogen, straight or branched $C_1$-$C_3$ alkyl and straight or branched $C_1$-$C_3$ alkoxy;

A is —NH—, —O—, —S—, —(C=O)NH—, —NH(C=O)—, (C=O)O— or —O(C=O)—; and m and n can independently be integers of 0-6.

Further, in formula 1 above, $R^1$ and $R^2$ are independently straight or branched $C_1$-$C_3$ alkyl, —$NO_2$, or nonsubstituted or substituted phenyl, wherein the substituted phenyl can be substituted with one or more substituents selected from the group consisting of straight or branched $C_1$-$C_3$ alkyl, straight or branched $C_1$-$C_3$ alkoxy and —$NO_2$;

$R^3$ is hydrogen, —(C=O)$OR^6$ or nonsubstituted or substituted 5-7 membered heterocycloalkyl containing one or more heteroatoms selected from the group consisting of N, O and S, at this time, the substituted heterocycloalkyl can be substituted with one or more straight or branched $C_1$-$C_3$ alkyl groups;

A is —(C=O)NH—, —NH(C=O)—, —(C=O)O— or —O(C=O)—; and m and n can independently be integers of 0-5.

Moreover, in formula 1 above, $R^1$ and $R^2$ are independently methyl or nonsubstituted or substituted phenyl, wherein the substituted phenyl can be substituted with one or more substituents selected from the group consisting of methyl, methoxy and —$NO_2$;

$R^3$ is —(C=O)OH or piperidinyl substituted with one or more methyl groups;

A is —(C=O)NH— or —NH(C=O)—; and m and n can independently be integers of 0-3.

The health functional food composition according to the present invention can be prepared by adding the compound of formula 1 above or the pharmaceutically acceptable salt thereof to food or beverages for the purpose of preventing or alleviating pruritus.

The food herein is not limited. For example, the composition of the present invention can be added to drinks, meats, sausages, breads, biscuits, rice cakes, chocolates, candies, snacks, pizza, ramyuns, flour products, gums, dairy products including ice cream, soups, beverages, alcohol drinks and vitamin complex, etc., and in wide sense, almost every health functional food can be included.

The compound represented by formula 1 of the present invention can be used as food additive. In that case, the compound can be added as it is or as mixed with other food components according to the conventional method. The mixing ratio of active ingredients can be regulated according to the purpose of use (prevention or alleviation). In general, the compound represented by formula 1 of the present invention can be added at 0.1 to 90 weight parts by the total food weight. However, if long term administration is required for health and hygiene or regulating health condition, the content can be lower than the above but higher content can be accepted as well since the compound has been proved to be very safe.

The composition for health beverages of the present invention can additionally include various flavors or natural carbohydrates, etc., like other beverages in addition to the compound. The natural carbohydrates above can be one of monosaccharides such as glucose and fructose; disaccharides such as maltose and sucrose; polysaccharides such as dextrin and cyclodextrin; and sugar alcohols such as xylitol, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1-20 g and more preferably 5-12 g in 100 g of the composition of the present invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The pyrazole derivative represented by formula 1 of the present invention can also include natural fruit juice, fruit beverages and fruit flesh addable to vegetable beverages. All the mentioned ingredients can be added singly or together. The mixing ratio of those ingredients does not matter in fact, but in general, each can be added by 0.1-20 weight part per 100 weight part of the pyrazole derivative represented by formula 1 of the present invention.

Further, the present invention provides a screening method of a compound for preventing or treating pruritus, which comprises the following steps:
treating a pruritus-inducing substance to cells expressing MRGPR X1 (Mas-related G protein-coupled receptor), and culturing the cells (step 1); and
treating a candidate material to the pruritus-induced cells, and measuring the inhibition of MRGPR X1 activity (step 2).

At this time, the pruritus-inducing substance of step 1 can be chloroquine, and any histamine-independent pruritus-inducing substance which is not mediated by histamine can be used without limitation. On the other hand, the pruritus-inducing substance can be an acute pruritus-inducing substance.

In addition, the present invention provides a screening method of an active material for preventing or treating pruritus, which comprises the following steps:
treating a pruritus-inducing substance to cells expressing hH1R (human Histamine 1 Receptor), and culturing the cells (step 1); and
treating a candidate material to the pruritus-induced cells, and measuring the inhibition of hH1R activity (step 2).

At this time, the pruritus-inducing substance of step 1 can be one or more substances selected from the group consisting of histamine, interleukin-1, cytokine, serotonin, acetylcholine, substance P, leukotriene and prostaglandin, and any histamine-dependent pruritus-inducing substance can be used without limitation.

In the screening method according to the present invention, the measurement of step 2 can be performed by one or more methods selected from the group consisting of fluorescence assay, fluorescence resonance energy transfer assay, bioluminescence resonance energy transfer assay, fluorescence polarization assay, Western blotting, immunoprecipitation assay, dual luciferasereporter assay, enzyme-linked immunosorbent assay (ELISA) and immunohistochemistry, and any measurement method commonly used in the art can be used without limitation.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Example 1> Pharmaceutical Composition for Preventing or Treating Pruritus A pharmaceutical composition comprising the pyrazole derivative represented by formula 2 for preventing or treating pruritus was prepared in Experimental Example 1. At this time, the pyrazole derivative represented by formula 2 was purchased from Com Genex (CAS Number. 1023449-28-6).

[Formula 2]

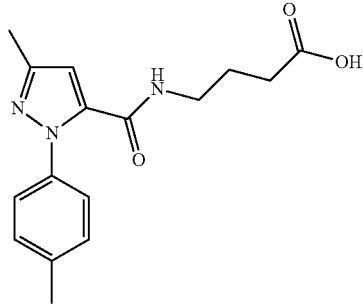

<Experimental Example 1> Screening of Active Material for Preventing or Treating Pruritus The following experiment was performed using the screening method of the present invention in order to find a compound suitable for the prevention or treatment of pruritus.

1. MRGPR X1 Stable Cell Line 제조
 1. Preparation of MRGPR X1 Stable Cell Line
 Human MRGPRX1 gene was sub-cloned in pcDNA5 FRT vector, which was transfected into HEK 293T FRT cells. The cells were cultured in a 37° C., 5% $CO_2$ incubator for 48 hours.
 To confirm the amount with which a single colony is well formed, the transfected cells were serially diluted and then transferred and distributed on 100 mm dish evenly. The medium was replaced with a fresh medium containing 50/g/mℓ of hygromycin every 3-4 days. The cells were cultured until colonies were formed.
 Once colonies were formed, only a single colony was transferred to a 24 well plate, followed by culture. Then, well grown cells were transferred to a 6 well plate, followed by culture. Antibiotic selection was performed. To select those cells which were not able to survive in Zeocin medium but were well grown in hygromycin medium, the cells were seeded in 6 well plates. A medium containing 50 μg/mℓ of Zeocin was added to one plate and a medium containing 50 μg/mℓ of hygromycin was added to the other plate. The cells that died in Zeocin medium but grew well in hygromycin medium were selected, with which PCR and β-galactosidase assay were performed to confirm the success of transfection.
 2. MRGPR X1 Screening Assay
 The following experiment was performed to find a material effective in pruritus using the Mrgpr X1 stable cell line prepared above.
 First, MRGPR X1 stable cells were counted to make 8000 cells/well, followed by seeding in a Poly-D-Lysine coated plate 384 well black/clear plate. Then, the cells were cultured in a 37° C., 5% $CO_2$ incubator for overnight.
 The subsequent procedure was performed using Biomex FX (Beckman). After eliminating the medium, flo-3 AM dye dissolved in Na-HEPES buffer (5 mM KCl, 2 mM $MgCl_2$, 140 mM NaCl, 10 mM NaOH-HEPES, pH7.2) at the concentration of 2.5 μM was added to the plate (25 μℓ/well), followed by culture in a 37° C., 5% $CO_2$ incubator for 30 minutes.
 During the culture, a compound plate was prepared. Particularly, a 6 mM original stock plate (96 plate form) was pre-mixed well and then an intermediate plate was prepared. Na-HEPES buffer containing 1 mM chloroquine dissolved therein was distributed in a 384 clear V bottom plate (49 μℓ/well) using Multidrop. Then, 1 μℓ was taken from the original stock plate (6 mM, 100% DMSO), which was diluted in the intermediate plate (120 uM compound, 1 mM chloroquine, 2% DMSO), leading to the preparation of a final compound plate.
 Na-HEPES buffer containing 1 mM chloroquine dissolved therein was distributed in the 384 clear plate (40 μℓ/well) using Multidrop, and 10 μℓ was taken from the intermediate plate, which was diluted in the final compound plate (24 μM compound, 1 mM chloroquine, 0.4% DMSO).
 Upon completion of the incubation, dye was discarded and Na-HEPES buffer was added thereto (25 μℓ/well) for washing, and then buffer was added thereto (25 μℓ/well) again. 25 μℓ of the primary candidate material was added to each well of the assay plate containing 25 μℓ of buffer, followed by reading the plate (final 12 μM compound, 500 μM chloroquine, 0.2% DMSO). Vehicle was treated by dissolving 500 μM chloroquine in 0.2% DMSO.
 The experimental results were analyzed using a microplate reader (Flexstaion $II^{384}$, Molecular Devices). Fluorescence assay was performed (Ex 488 nm, Em 535 nm) at the intervals of 3.2 seconds for 80 seconds. As a result, the compounds with good test results were sorted, based on which, 910 secondary candidate materials for the treatment of pruritus were selected.
 3. HumanHistamine1 Receptor Antagonist Assay
 Human histamine 1 receptor antagonist assay was performed with those 910 secondary candidate materials selected in the MRGPR X1 experiment above.
 HEK 293T cells were transiently transfected with 2 μg of human histamine 1 receptor, followed by seeding at the density of 4000 cells/well. The cells were cultured in a 37° C., 5% $CO_2$ incubator for 48 hours.
 The subsequent procedure was performed using Biomex FX. After eliminating the medium, flo-3 AM dye dissolved in Na-HEPES buffer (5 mM KCl, 2 mM $MgCl_2$, 140 mM NaCl, 10 mM NaOH-HEPES, pH7.2) at the concentration of 2.5 μM was added to the plate (25 μℓ/well) of the vehicle and experimental groups, and flo-3 AM dye dissolved in Na-HEPES buffer containing 5 uM diphenhydramine dissolved therein at the concentration of 2.5 μM was added to the plate (25 μℓ/well) of the control group, followed by culture in a 37° C., 5% $CO_2$ incubator for 30 minutes.
 During the culture, a compound plate was prepared. Particularly, a 6 mM original stock plate (96 plate form) was pre-mixed well and then an intermediate plate was prepared. Na-HEPES buffer containing 2 μM histamine dissolved therein was distributed in a 384 clear V bottom plate (49 μℓ/well) using Multidrop. Then, 1 μℓ was taken from the μℓ original stock plate (6 mM, 100% DMSO), which was diluted in the intermediate plate (120 μM compound, 2 μM histamine, 2% DMSO), leading to the preparation of a final compound plate.
 Na-HEPES buffer containing 2 μM histamine dissolved therein was distributed in the 384 clear plate (40 μℓ/well) using Multidrop, and 10 μℓ was taken from the intermediate plate, which was diluted in the final compound plate (24 μM compound, 2 μM histamine, 0.4% DMSO, excluding control group wells).
 Upon completion of the incubation, dye was discarded and Na-HEPES buffer was added thereto (25 μℓ/well) for washing, and then buffer was added thereto (25 μℓ/well) again (excluding control group wells). Na-HEPES buffer containing 5 μM diphenhydramine and 2 μM histamine dissolved therein was added to the control group wells (25 μℓ/well). Finally, 25 μℓ of the compound was added to each well of the assay plate containing 25 μℓ of buffer, followed by reading the plate (final 12 μM compound, 1 μM histamine, 0.2% DMSO).
 The experimental results were analyzed using a microplate reader (Flexstaion $II^{384}$, Molecular Devices). Fluorescence assay was performed (Ex 488 nm, Em 535 nm) at the intervals of 3.2 seconds for 80 seconds. As a result, 25 compounds having excellent effects were selected from the 910 compounds selected above. A few kinds of scaffolds representing the similarity in their structures were identified. Among them, 4 kinds of compounds having the representative structure were derived. At last, compound #3 which was confirmed to be excellent in treating pruritus and at the same time having excellent solubility in blood was selected as a final therapeutic material for pruritus. Compound #3 is a compound represented by formula 2 of Example 1.
 4. Analysis of Experiment Results
 To evaluate the activity of Mrgpr X1 expressing cells and hH1R expressing cells according to compound #3, the final therapeutic material for pruritus, data collected from the experiments above were compared and analyzed.

Figure 2:
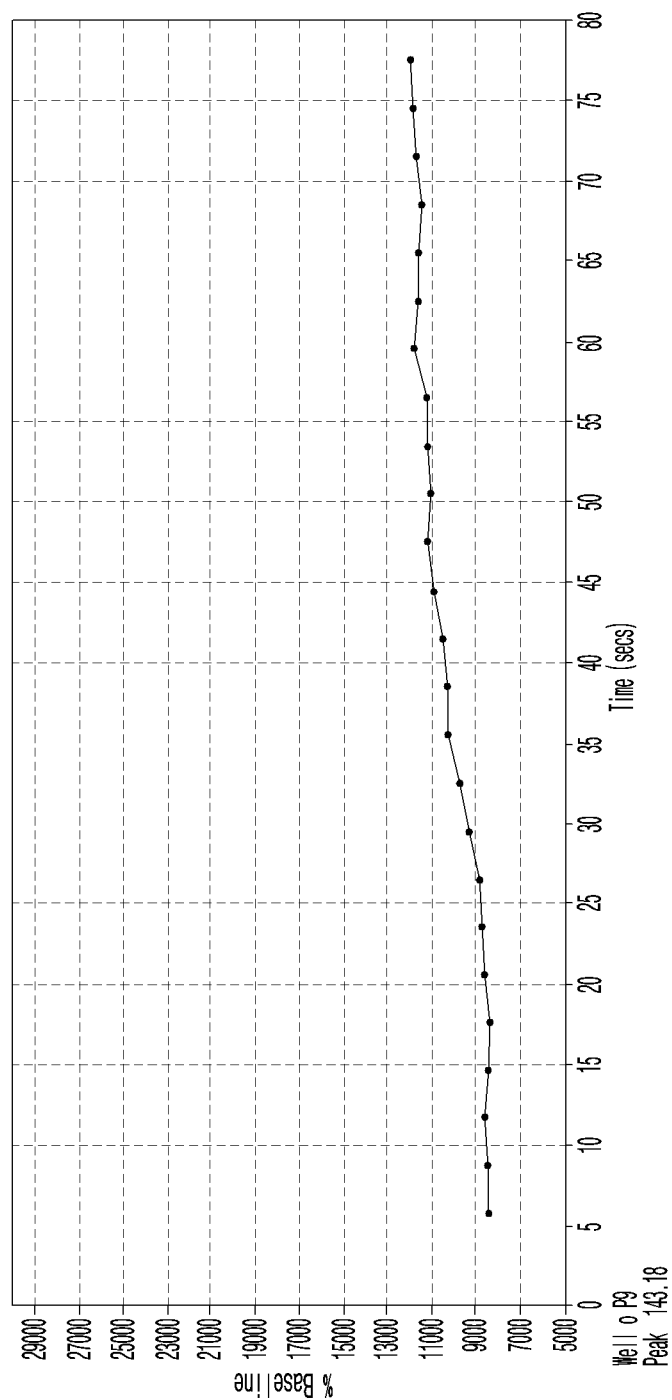
FIG. 2 is a graph showing the results of fluorescence analysis performed after treating Mrgpr X 1 cells with a pharmaceutical composition comprising the pyrazole derivative of Example 1 together with chloroquine.

FIG. 1 is a graph showing the results of fluorescence analysis performed after treating Mrgpr X1 cells with chloroquine alone, and FIG. 2 is a graph showing the results of fluorescence analysis performed after treating Mrgpr X 1 cells with a pharmaceutical composition comprising the pyrazole derivative of Example 1 together with chloroquine.

As shown in FIG. 1 and FIG. 2, fluorescence analysis result was declined approximately 54% when the pharmaceutical composition of the present invention was co-treated with chloroquine, compared with when chloroquine was treated alone.

Therefore, the pharmaceutical composition for preventing or treating pruritus according to the present invention can be effectively used as a preventive or therapeutic agent for non-histaminergic pruritus since it can relieve the symptoms of pruritus by inhibiting the activity of intracellular Mrgpr X1.

Figure 3:
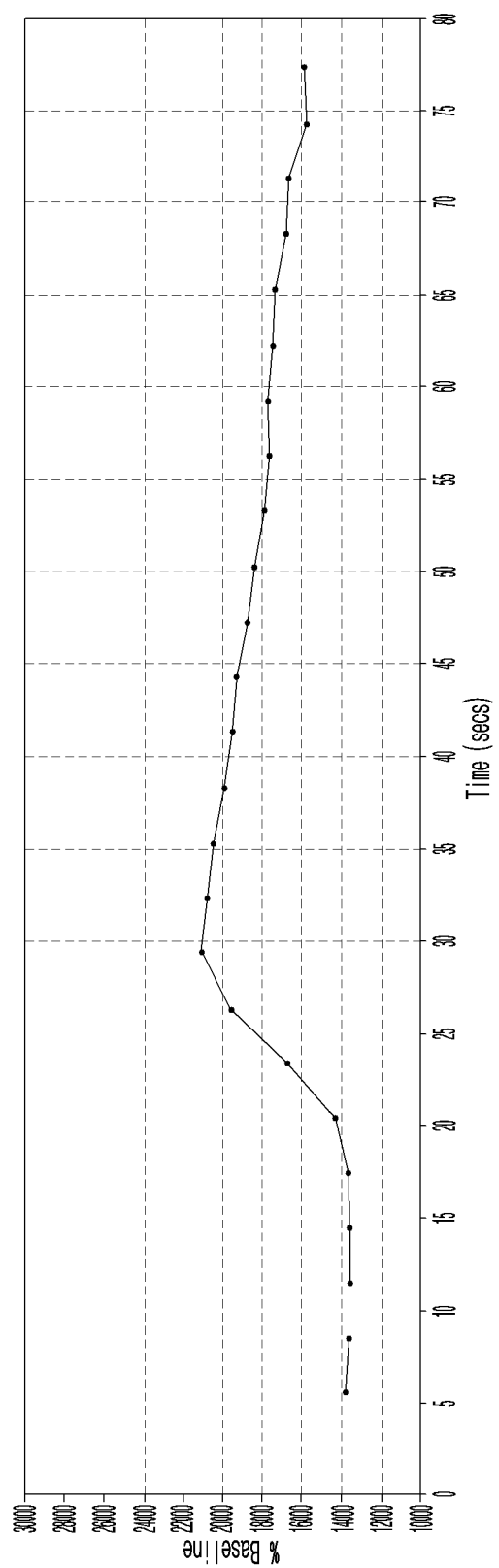
FIG. 3 is a graph showing the results of fluorescence analysis performed after treating hH1R cells with histamine alone.
Figure 4:
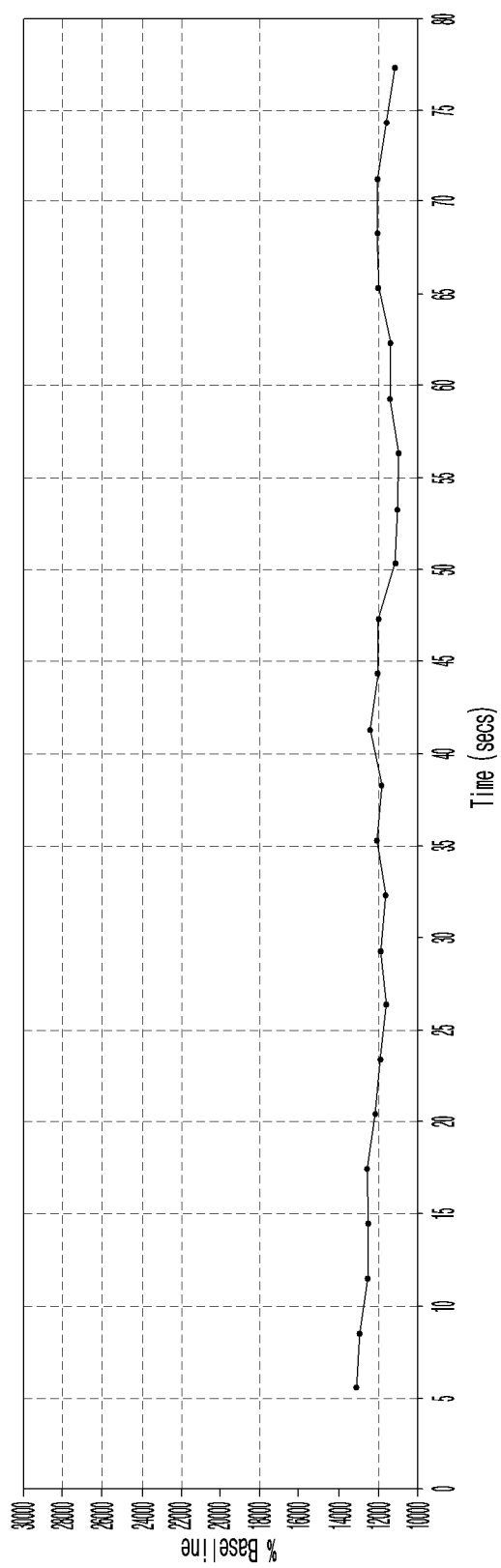
FIG. 4 is a graph showing the results of fluorescence analysis performed after treating hH1R cells with histamine and diphenhydramine.
Figure 5:
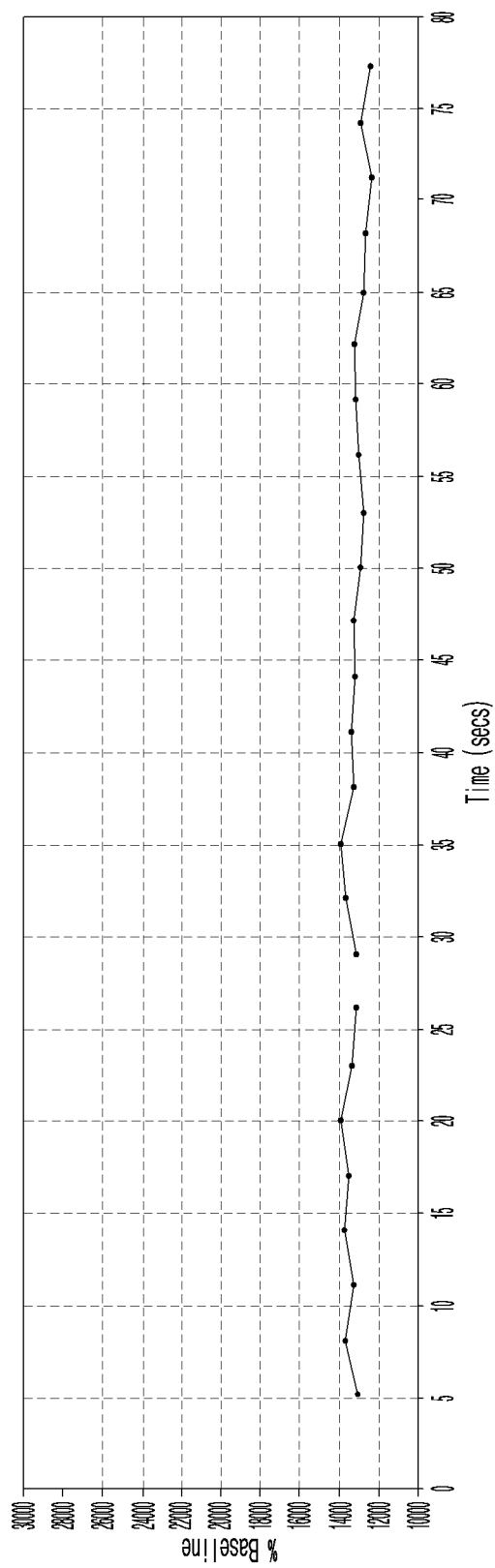
FIG. 5 is a graph showing the results of fluorescence analysis performed after treating hH1R cells with a pharmaceutical composition comprising the pyrazole derivative of Example 1 together with histamine.

FIG. 3 is a graph showing the results of fluorescence analysis performed after treating hH1R cells with histamine alone, FIG. 4 is a graph showing the results of fluorescence analysis performed after treating hH1R cells with histamine and diphenhydramine, and FIG. 5 is a graph showing the results of fluorescence analysis performed after treating hH1R cells with a pharmaceutical composition comprising the pyrazole derivative of Example 1 together with histamine.

As shown in FIGS. 3~5, the pharmaceutical composition of the present invention was able to reduce approximately 94%, considering the inhibition effect when histamine and diphenhydramine (H1 receptor antagonist) were treated together as 100%.

Therefore, the pharmaceutical composition for preventing or treating pruritus according to the present invention can be effectively used as a preventive or therapeutic agent for histaminergic pruritus since it can relieve the symptoms of pruritus by inhibiting the activity of intracellular hH1R.

<Experimental Example 2> Animal Model Experiment of the Therapeutic Agent for Pruritus of the Present Invention To confirm the in vivo treatment effect of the pharmaceutical composition for treating pruritus of the present invention, pruritus evaluation in the histamine mouse model, pruritus evaluation in the chloroquine mouse model, pruritus evaluation in the dry skin mouse model, pruritus evaluation in the psoriasis mouse model and mouse motor ability test were performed.

1. Pruritus Evaluation in Histamine Mouse Model

An experiment was performed as follows in order to evaluate the pruritus treatment effect of the pharmaceutical composition of Example 1 in the histamine mouse model.

Seven week-old C57BL6 mice were placed in a new cage and adapted for 30 minutes before starting the experiment. As for the control group, 3% DMSO was dissolved in physiological saline (0.9% saline), which was intraperitoneally injected (50 µℓ /mouse). The animal model mice were intraperitoneally injected with the pharmaceutical composition of Example 1 (30 mg/kg) dissolved in physiological saline (0.9% saline) containing 3% DMSO (50 µℓ /mouse). The mice were also µℓ placed in the same cage above for 30 minutes.

Then, control and animal model mice were subcutaneously injected with 500 µg/50 µℓ of histamine on the dorsal side, and their behaviors were recorded with a digital video camera for 30 minutes. The number of scratches was recorded while playing back the recorded video file on a computer. A continuous action of scratching the skin from when the mouse lifted its hind foot off the floor and to when the mouse put it back on the floor was considered 1 scratch, and the number of scratches counted for 30 minutes was used as index for evaluating pruritus.

Figure 6:
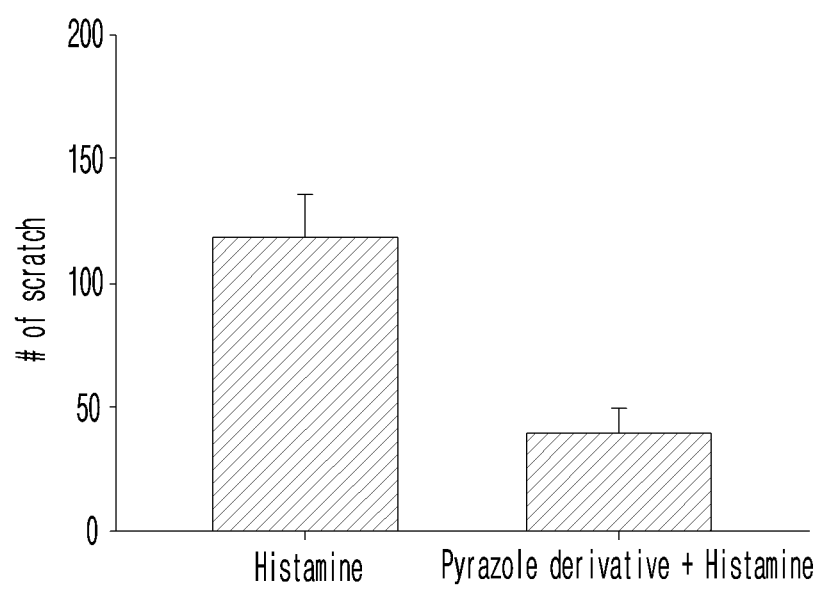
FIG. 6 is a graph illustrating the evaluation of pruritus treatment effect when the histamine mouse model is treated with a pharmaceutical composition comprising the pyrazole derivative of Example 1.

FIG. 6 is a graph illustrating the evaluation of pruritus treatment effect when the histamine mouse model is treated with a pharmaceutical composition comprising the pyrazole derivative of Example 1.

As shown in FIG. 6, the average number of total scratches accumulated for 30 minutes in the control group was 118.38 times, and the average number of scratches in the experimental group administered with the pharmaceutical composition of the present invention was 39.90 times.

Therefore, the pharmaceutical composition comprising the pyrazole derivative according to the present invention can be effectively used as a pharmaceutical composition for treating or preventing pruritus since it showed an effect of reducing histaminergic pruritus.

2. Pruritus Evaluation in Chloroquine Mouse Model

An experiment was performed as follows in order to evaluate the pruritus treatment effect of the pharmaceutical composition of Example 1 in the chloroquine mouse model.

Seven week-old C57BL6 mice were placed in a new cage and adapted for 30 minutes before starting the experiment. As for the control group, 3% DMSO was dissolved in physiological saline (0.9% saline), which was intraperitoneally injected (50 µℓ /mouse). The animal model mice were intraperitoneally injected with the pharmaceutical composition of Example 1 (30 mg/kg) dissolved in physiological saline (0.9% saline) containing 3% DMSO (50 µℓ /mouse). The mice were also µℓ placed in the same cage above for 30 minutes.

Then, control and animal model mice were subcutaneously injected with 200 µg/50 µℓ of chloroquine on the dorsal side, and their behaviors were recorded with a digital video camera for 30 minutes. The number of scratches was recorded while playing back the recorded video file on a computer. A continuous action of scratching the skin from when the mouse lifted its hind foot off the floor and to when the mouse put it back on the floor was considered 1 scratch, and the number of scratches counted for 30 minutes was used as index for evaluating pruritus.

Figure 7:
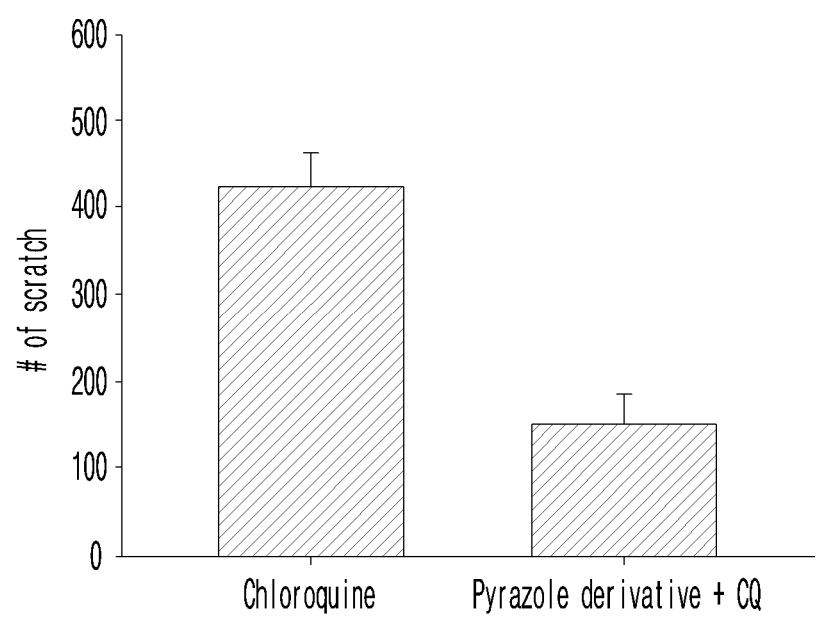
FIG. 7 is a graph illustrating the evaluation of pruritus treatment effect when the chloroquine mouse model is treated with a pharmaceutical composition comprising the pyrazole derivative of Example 1.

FIG. 7 is a graph illustrating the evaluation of pruritus treatment effect when the chloroquine mouse model is treated with a pharmaceutical composition comprising the pyrazole derivative of Example 1.

As shown in FIG. 7, the average number of total scratches accumulated for 30 minutes in the control group was 425.00 times, and the average number of scratches in the experimental group administered with the pharmaceutical composition of the present invention was 150.50 times.

Therefore, it was confirmed from the above results that the pharmaceutical composition comprising the pyrazole derivative compound according to the present invention was significantly effective in not only alleviating histaminergic pruritus but also alleviating non-histaminergic pruritus, suggesting that the composition of the present invention can be effectively used for the treatment of non-histaminergic pruritus.

3. Pruritus Evaluation in Dry Skin Mouse Model

An experiment was performed as follows in order to evaluate the pruritus treatment effect of the pharmaceutical composition of Example 1 in the dry skin mouse model.

First, a dry skin mouse model was constructed. A dry skin mouse model was prepared according to the instruction described Jpn J Pharmacol. 2002 March; 88(3):285-92. ENTOBAR® was mixed with physiological saline (0.9% saline) at the ratio of 1:1, which was intraperitoneally injected in 7-week-old $C_{57}BL6$ mice (20 µℓ /mouse) to anesthetize the mice. Then, the hair of the right nape was shaved using a clipper. Ethyl ether and acetone were mixed at the ratio of 1:1. The mixture was soaked in absorbent cotton and the right nape was rubbed with the absorbent cotton for 1 minute. Then, absorbent cotton soaked with water was used to rub in the same way. This process was performed once in the morning and once in the afternoon for 5 days.

Next, pruritus evaluation in the dry skin mouse model was performed. In the afternoon on Day 5, the control group mice were intraperitoneally injected with 3% DMSO dissolved in physiological saline (0.9% saline) (50 µℓ /mouse). The animal model mice were intraperitoneally injected with the pharmaceutical composition of Example 1 (30 mg/kg) dissolved in physiological saline (0.9% saline) containing 3% DMSO (50 µℓ /mouse). The mice were also placed in the same cage for 30 minutes. 30 minutes later, their behaviors were recorded with a digital camera for 30 minutes. The number of scratches was recorded while playing back the recorded video file on a computer. A continuous action of scratching the skin from when the mouse lifted its hind foot off the floor and to when the mouse put it back on the floor was considered 1 scratch, and the number of scratches counted for 30 minutes was used as index for evaluating pruritus.

Figure 8:
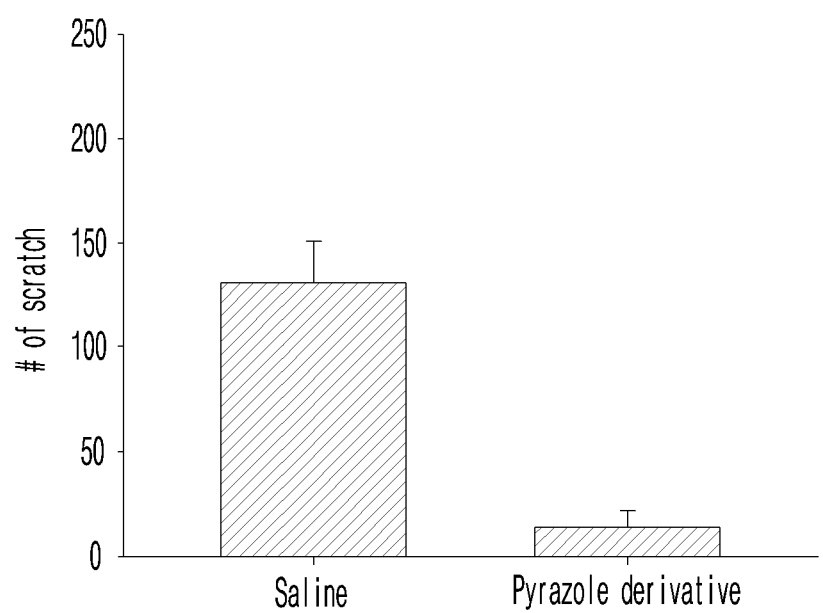
FIG. 8 is a graph illustrating the evaluation of pruritus treatment effect when the dry skin mouse model is treated with a pharmaceutical composition comprising the pyrazole derivative of Example 1.

FIG. 8 is a graph illustrating the evaluation of pruritus treatment effect when the dry skin mouse model is treated with a pharmaceutical composition comprising the pyrazole derivative of Example 1.

As shown in FIG. 8, the average number of total scratches accumulated for 30 minutes in the control group was 130.00 times, and the average number of total scratches in the experimental group administered with the pharmaceutical composition of the present invention was 14.00 times.

Therefore, it was confirmed from the above results that the pharmaceutical composition comprising the pyrazole derivative compound according to the present invention was significantly effective in alleviating pruritus induced by dry skin, suggesting that the composition of the present invention can be effectively used for the treatment of pruritus induced by dry skin or dry skin.

4. Evaluation of Rota Rod Motor Condition

To evaluate the in vivo stability of the pharmaceutical composition according to the present invention, Rota rod motion condition test was performed with a mouse model.

The test mouse was placed on the Rota rod device and then the speed was raised from 4 to 40 until the mouse fell. When the mouse fell, it was moved to a cage. The procedure was repeated three times a day for 3 consecutive days to adapt the mouse to the Rota rod device. After three days of adaptation, the mouse was moved to a cage where it was stabilized.

As for the control group, 3% DMSO was dissolved in physiological saline (0.9% saline), which was intraperitoneally injected (50 µℓ /mouse). The animal model mice were intraperitoneally injected with the pharmaceutical composition of Example 1 (30 mg/kg) dissolved in physiological saline (0.9% saline) containing 3% DMSO (50 µℓ /mouse). The mice were also placed in the same cage above for 30 minutes. The experiment above was repeated three times like the adaptation test above, and the average time of falling was calculated.

Figure 9:
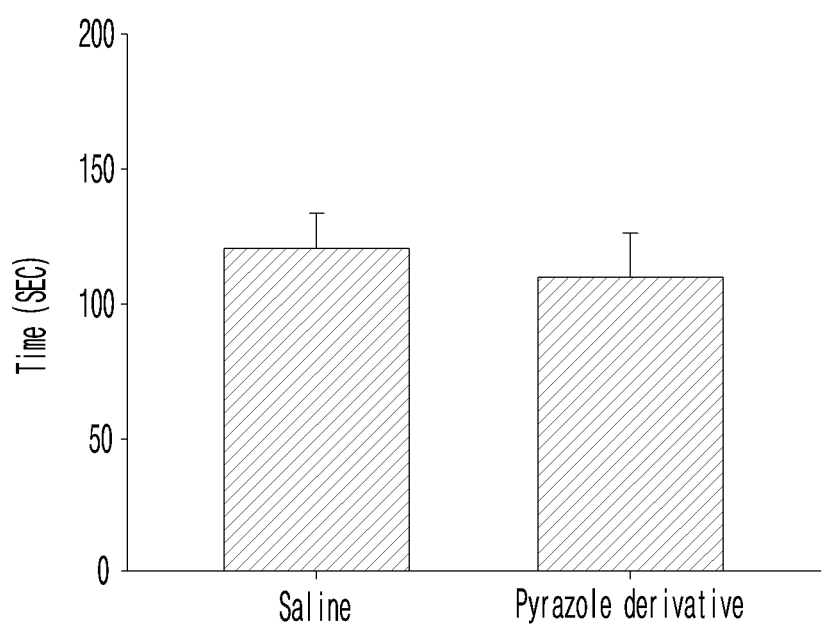
FIG. 9 is a graph showing the results of Rota rod motion condition test with the mouse treated with a pharmaceutical composition comprising the pyrazole derivative of Example 1.

FIG. 9 is a graph showing the results of Rota rod motion condition test with the mouse treated with a pharmaceutical composition comprising the pyrazole derivative of Example 1.

As shown in FIG. 9, when comparing the motor condition ability between the control group and the experimental group administered with the pharmaceutical composition of the present invention, there was no significant difference between the groups.

Therefore, the pharmaceutical composition containing the pyrazole derivative according to the present invention was confirmed not to cause any adverse reaction in vivo when administered, but to maintain a stable activity, so that the composition can be effectively used as a pharmaceutical composition for preventing or treating pruritus.

5. Pruritus Evaluation in Psoriatic Mouse Model

An experiment was performed as follows in order to evaluate the pruritus treatment effect of the pharmaceutical composition of Example 1 in the psoriatic mouse model.

First, a psoriatic mouse model was constructed. A psoriatic mouse model was prepared according to the instruction described Pain. 2016 November; 2536-2543. Zoletil (15 mg/kg) was mixed with saline at the ratio of 1:1 and then mixed with Rompun (5 mg/kg), which was intraperitoneally injected in 7-week-old C57BL6 mice to anesthetize the mice. The mouse back was primarily depilated in the size of 2.5×2 cm using a clipper, and then secondly depilated using a straight blade. Vaseline cream was rubbed on the depilated area of the normal group for 7 days using a cotton swap. Aldara cream (62.5 mg, 5% imiquimod) was rubbed on the depilated area of the control group and the experimental group for 7 days using a cotton swap.

Next, pruritus evaluation in the psoriatic mouse model was performed. On day 8, the normal group and control group mice were intraperitoneally injected with 3% DMSO dissolved in physiological saline (0.9% saline) (50 µℓ /mouse). The experimental group mice were intraperitoneally injected with the pharmaceutical composition of Example 1 (30 mg/kg) dissolved in physiological saline (0.9% saline) containing 3% DMSO (50 µℓ /mouse). The mice were placed in the same cage for 30 minutes. 30 minutes later, their behaviors were recorded with a digital camera for 30 minutes. The number of scratches was recorded while playing back the recorded video file on a computer. A continuous action of scratching the skin from when the mouse lifted its hind foot off the floor and to when the mouse put it back on the floor was considered 1 scratch, and the number of scratches counted for 30 minutes was used as index for evaluating pruritus.

Figure 10:
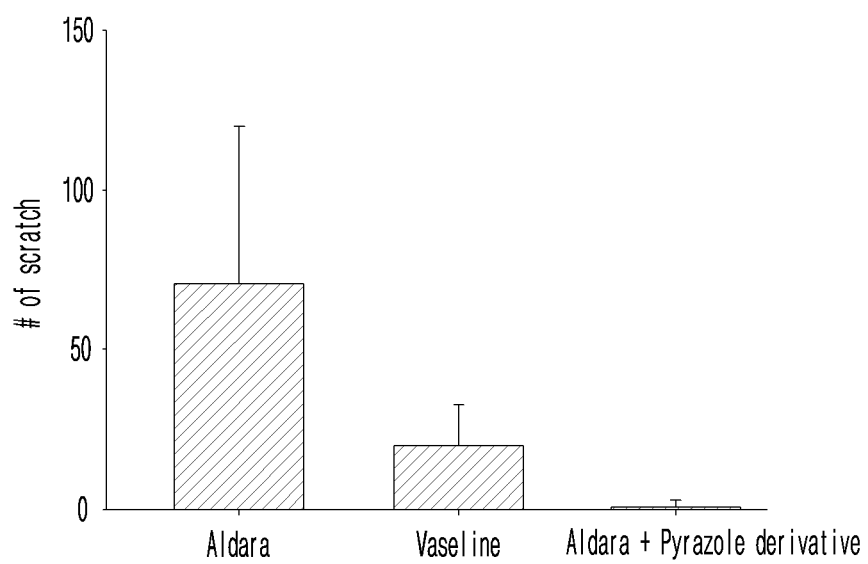
FIG. 10 is a graph illustrating the evaluation of pruritus treatment effect when the psoriatic mouse model is treated with a pharmaceutical composition comprising the pyrazole derivative of Example 1.

FIG. 10 is a graph illustrating the evaluation of pruritus treatment effect when the psoriatic mouse model is treated with a pharmaceutical composition comprising the pyrazole derivative of Example 1.

As shown in FIG. 10, the average number of total scratches accumulated in the normal group was 20.00 times, and the average number of total scratches in the control group (Aldara cream treated group) was 71.00 times. In the group administered with the pharmaceutical composition containing the pyrazole derivative according to the present invention, the average number of total scratches was 1.00, indicating the scratch times were significantly reduced.

Therefore, it was confirmed from the above results that the pharmaceutical composition comprising the pyrazole derivative according to the present invention was significantly effective in alleviating pruritus induced by psoriasis, suggesting that the composition of the present invention can be effectively used for the treatment of pruritus induced by psoriasis or psoriasis.

<Manufacturing Example 1> Preparation of Powders

| | |
|---|---|
| Compound represented by formula 1 | 2 g |
| Lactose | 1 g |

Powders were prepared by mixing all the above components, which were filled in airtight packs according to the conventional method for preparing powders.

<Manufacturing Example 2> Preparation of Tablets

| | |
|---|---|
| Compound represented by formula 1 | 100 mg |
| Corn starch | 100 mg |
| Lactose | 100 mg |
| Magnesium stearate | 2 mg |

Tablets were prepared by mixing all the above components by the conventional method for preparing tablets.

<Manufacturing Example 3> Preparation of Capsules

| | |
|---|---|
| Compound represented by formula 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<Manufacturing Example 4> Preparation of Injectable Solutions

| | |
|---|---|
| Compound represented by formula 1 | 100 mg |
| Mannitol | 180 mg |
| $Na_2HPO_4 \cdot 2H_2O$ | 26 mg |
| Distilled water | 2974 mg |

Injectable solutions were prepared by containing all the above components in the amounts indicated according to the conventional method for preparing injectable solutions.

<Manufacturing Example 5> Preparation of Ointments

| | |
|---|---|
| Compound represented by formula 1 | 5 g |
| Cetyl palmitate | 20 g |
| Cetanol | 40 g |
| Stearyl alcohol | 40 g |
| Myristan isopropyl | 80 g |
| Polysorbate | 60 g |
| Propyl p-hydroxybenzoate | 1 g |
| Methyl p-hydroxybenzoate | 1 g |

Phosphoric Acid and Purified Water Proper Amount

Ointments were prepared by containing all the above components in the amounts indicated according to the conventional method for preparing ointments.

<Manufacturing Example 6> Preparation of Health Functional Foods

| | |
|---|---|
| Compound represented by formula 1 | 500 ng |
| Vitamin complex | proper amount |
| Vitamin A acetate | 70 mg |
| Vitamin E | 1.0 mg |
| Vitamin | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinamide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate | 15 mg |
| Calcium phosphate, dibasic | 55 mg |
| Potassium citrate | 90 mg |
| Calcium carbonate | 100 mg |
| Magnesium chloride | 24.8 mg |

The vitamins and minerals appropriate for health functional foods were mixed according to the preferred mixing ratio but the composition ratio can be adjusted arbitrarily. After mixing the above components according to the conventional method for preparing health functional foods, granules were prepared and the granules were used for the preparation of health functional foods according to the conventional method.

<Manufacturing Example 7> Preparation of Health Beverages

| | |
|---|---|
| Compound represented by formula 1 | 500 ng |
| Citric acid | 1000 mg |
| Oligosaccharide | 100 g |
| Maesil (Prunus mume) Extract | 2 g |
| Taurine | 1 g |
| Purified water | up to 900 ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and ethnic preferences such as demand class, demand country, and purpose of use, etc.

INDUSTRIAL APPLICABILITY

The pharmaceutical composition for preventing or treating pruritus according to the present invention can be effectively used as a preventive or therapeutic agent for non-histaminergic pruritus, a preventive or therapeutic agent for histaminergic pruritus, a therapeutic agent for dry skin and a therapeutic agent for psoriasis.

What is claimed is:

1. A method of treating or improving pruritus, the method comprising administering to a subject in need an effective amount of a compound represented by formula 2 below or a pharmaceutically acceptable salt thereof:

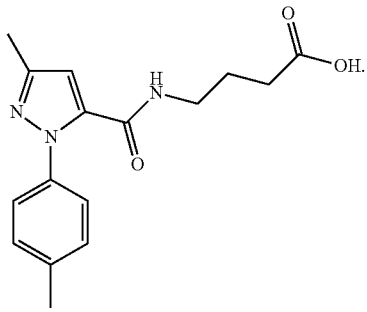

Formula 2

2. The method of treating or improving pruritus according to claim 1, wherein the pruritus is histaminergic pruritus.

3. The method of treating or improving pruritus according to claim 1, wherein the pruritus is non-histaminergic pruritus.

4. The method of treating or improving pruritus according to claim 1, wherein the pruritus is a pruritus induced by one or more diseases selected from the group consisting of psoriasis, dry skin, neurodermatitis, contact dermatitis, seborrheic dermatitis, autosensitized dermatitis, caterpillar dermatitis, sebum deficiency (asteatosis), senile pruritus skin, insect bites, photosensitive dermatitis, urticaria, prurigo, herpes, impetigo, eczema, tinea, lichen, scabies and acne vulgaris.

* * * * *